(12) United States Patent
Ishimura (10) Patent No.: US 11,697,627 B2
(45) Date of Patent: Jul. 11, 2023

(54) METHOD OF SEPARATING DOUBLE BOND-CONTAINING LINEAR HYDROCARBON IN WHICH EVERY HYDROGEN ATOM IS REPLACED WITH FLUORINE ATOM OR CHLORINE ATOM

(71) Applicant: ZEON CORPORATION, Tokyo (JP)

(72) Inventor: Takayuki Ishimura, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 126 days.

(21) Appl. No.: 17/595,090

(22) PCT Filed: May 13, 2020

(86) PCT No.: PCT/JP2020/019161
§ 371 (c)(1),
(2) Date: Nov. 9, 2021

(87) PCT Pub. No.: WO2020/235425
PCT Pub. Date: Nov. 26, 2020

(65) Prior Publication Data
US 2022/0213010 A1    Jul. 7, 2022

(30) Foreign Application Priority Data

May 20, 2019    (JP) .................................. 2019-094805

(51) Int. Cl.
*C07C 17/42*    (2006.01)
(52) U.S. Cl.
CPC .................................. *C07C 17/42* (2013.01)
(58) Field of Classification Search
CPC ......... C07C 17/42; C07C 17/35; C07C 21/18; C07C 21/19; C07C 21/215; Y02C 20/30
See application file for complete search history.

(56) References Cited

U.S. PATENT DOCUMENTS

2003/0026743 A1    2/2003    Imamura
2013/0230929 A1    9/2013    Nakamura et al.

FOREIGN PATENT DOCUMENTS

JP    2000342931 A    12/2000
JP    2001302551 A    10/2001
(Continued)

OTHER PUBLICATIONS

Nov. 16, 2021, International Preliminary Report on Patentability issued in the International Patent Application No. PCT/JP2020/019161.

*Primary Examiner* — Jafar F Parsa
(74) *Attorney, Agent, or Firm* — Kenja IP Law PC (57) ABSTRACT

The object is to selectively separate a linear compound from a treatment subject containing linear and alicyclic compounds as double bond-containing hydrocarbon compounds in which every hydrogen is replaced with fluorine or chlorine. A method of separating a double bond-containing linear hydrocarbon in which every hydrogen is replaced with fluorine or chlorine includes bringing a treatment subject containing a double bond-containing linear hydrocarbon in which every hydrogen is replaced with fluorine or chlorine and a double bond-containing alicyclic hydrocarbon in which every hydrogen is replaced with fluorine or chlorine into contact with at least one amine compound selected from the group consisting of a heterocyclic aromatic amine compound and a tertiary amine represented by a formula: $NR^1R^2R^3$ ($R^1$, $R^2$, and $R^3$ are each independently an alkyl group, and two thereof may in combination form an alkylene group that is optionally interrupted by oxygen or sulfur).

14 Claims, 2 Drawing Sheets

(56) References Cited

FOREIGN PATENT DOCUMENTS

| | | | |
|---|---|---|---|
| JP | 2001324492 | A | 11/2001 |
| JP | 2012121018 | A | 6/2012 |
| WO | 2012002239 | A1 | 1/2012 |

FIG. 2

METHOD OF SEPARATING DOUBLE BOND-CONTAINING LINEAR HYDROCARBON IN WHICH EVERY HYDROGEN ATOM IS REPLACED WITH FLUORINE ATOM OR CHLORINE ATOM

TECHNICAL FIELD

The present disclosure relates to a method of separating a double bond-containing linear hydrocarbon in which every hydrogen atom is replaced with a fluorine atom or a chlorine atom from a treatment subject that contains a double bond-containing linear hydrocarbon in which every hydrogen atom is replaced with a fluorine atom or a chlorine atom and a double bond-containing alicyclic hydrocarbon in which every hydrogen atom is replaced with a fluorine atom or a chlorine atom.

BACKGROUND

Progress has been made in the development of double bond-containing perfluorocarbons as ingredients for fluororesins and as alternatives to saturated perfluorocarbons such as tetrafluoromethane ($CF_4$) and hexafluoroethane ($C_2H_6$) that have been used as etching gases and cleaning gases in production processes of semiconductors and liquid crystals. Double bond-containing perfluorocarbons are strictly regulated due to having global warming potential of a level that, despite being improved, cannot be disregarded, and also due to problems such as high vapor pressure and toxicity. For this reason, various proposals have been made in relation to methods of detecting and removing double bond-containing perfluorocarbons (Patent Literature (PTL) 1 to 5).

CITATION LIST

Patent Literature

PTL 1: JP2001-324492A
PTL 2: JP2001-302551A
PTL 3: JP2000-342931A
PTL 4: JP2012-121018A
PTL 5: WO2012/002239A1

SUMMARY

Technical Problem

The conventional techniques indicated above each treat double bond-containing perfluorocarbons collectively as a target of detection or removal and do not focus on the individual compounds included among double bond-containing perfluorocarbons. The characteristics of double bond-containing perfluorocarbons can differ depending on the skeleton of the compound (for example, whether the compound is linear, alicyclic, etc.). Therefore, the ability to selectively separate or remove a compound included among double bond-containing perfluorocarbons based on the skeleton of the compound would be useful in terms of enabling reuse, for example.

Solution to Problem

The inventor conducted diligent studies focusing on the skeletons of double bond-containing perfluorocarbons. The inventor discovered that when a linear compound and an alicyclic compound are included among double bond-containing perfluorocarbons, the linear compound can be selectively separated by bringing a specific amine compound into contact with the double bond-containing perfluorocarbons. The inventor also discovered that this finding is applicable not only to perfluorocarbons, but also to hydrocarbon compounds that are completely substituted with chlorine atoms and hydrocarbon compounds that are completely substituted with fluorine and chlorine atoms. The present disclosure was completed in light of these findings.

Specifically, the present disclosure relates to a method of separating a double bond-containing linear hydrocarbon in which every hydrogen atom is replaced with a fluorine atom or a chlorine atom, comprising bringing a treatment subject containing a double bond-containing linear hydrocarbon in which every hydrogen atom is replaced with a fluorine atom or a chlorine atom and a double bond-containing alicyclic hydrocarbon in which every hydrogen atom is replaced with a fluorine atom or a chlorine atom into contact with at least one amine compound selected from the group consisting of a heterocyclic aromatic amine compound and a tertiary amine represented by a formula: $NR^1R^2R^3$, where $R^1$, $R^2$, and $R^3$ are each independently an alkyl group, and two among $R^1$, $R^2$, and $R^3$ may in combination form an alkylene group that is optionally interrupted by an oxygen atom or a sulfur atom.

The term "double bond" as used in the present specification refers to a carbon-carbon double bond.

The phrase "replaced with a fluorine atom or a chlorine atom" as used in the present specification is inclusive of a case in which the replacement is with only fluorine atoms, a case in which the replacement is with both fluorine and chlorine atoms, and a case in which the replacement is with only chlorine atoms.

The term "perfluoro" as used in the present specification refers to a compound in which every hydrogen atom of a hydrocarbon is replaced with a fluorine atom.

The term "heterocyclic aromatic amine compound" as used in the present specification refers to an amine compound that includes a nitrogen atom among ring-forming atoms of a heteroaromatic ring.

Double bond-containing hydrocarbon compounds in which every hydrogen atom is replaced with a fluorine atom or a chlorine atom are generally difficult to selectively separate or remove by methods such as distillation purification and adsorption treatment because they have high reactivity as a result of including a double bond and often have similar boiling points to one another and high vapor pressures. The presently disclosed method makes it possible to separate a double bond-containing linear hydrocarbon in which every hydrogen atom is replaced with a fluorine atom or a chlorine atom from a treatment subject containing a double bond-containing linear hydrocarbon in which every hydrogen atom is replaced with a fluorine atom or a chlorine atom and a double bond-containing alicyclic hydrocarbon in which every hydrogen atom is replaced with a fluorine atom or a chlorine atom through a simple method of bringing the treatment subject into contact with a specific amine compound, and is also useful for reuse and the like. The presently disclosed separation method can also be used as a method of removing a double bond-containing alicyclic hydrocarbon in which every hydrogen atom is replaced with a fluorine atom or a chlorine atom from the aforementioned treatment subject.

The presently disclosed method separates a double bond-containing linear hydrocarbon in which every hydrogen atom is replaced with a fluorine atom or a chlorine atom by exploiting the fact that when a treatment subject that contains a double bond-containing linear hydrocarbon in which every hydrogen atom is replaced with a fluorine atom or a chlorine atom and a double bond-containing alicyclic hydrocarbon in which every hydrogen atom is replaced with a fluorine atom or a chlorine atom is brought into contact with a specific amine compound, the double bond-containing alicyclic hydrocarbon in which every hydrogen atom is replaced with a fluorine atom or a chlorine atom selectively reacts.

In the presently disclosed method, the amine compound that the treatment subject is brought into contact with is preferably in the form of a liquid. The amine compound that is in the form of a liquid may be a liquid phase amine compound or may be in the form of a liquid resulting from dissolution or dispersion of the amine compound in a solvent. The use of an amine compound that is in a liquid phase during contacting with the treatment subject is preferable in terms that a reaction proceeds quickly through the amine compound being in a liquid phase.

The contacting of the treatment subject and the amine compound can be performed inside a reactor, and introduction of the treatment subject into the reactor in the form of a gas is preferable in terms that it is easy to finely adjust the introduced amount thereof and in terms of inhibiting runaway of the reaction. The treatment subject may be subjected to heating or the like such that it is a gas.

The contacting of the treatment subject and the amine compound is preferably performed at a lower temperature than a boiling point of the double bond-containing alicyclic hydrocarbon in which every hydrogen atom is replaced with a fluorine atom or a chlorine atom in terms that it is easy to cause smooth progression of the reaction to an end point. In a case in which a plurality of compounds are present as the double bond-containing alicyclic hydrocarbon in which every hydrogen atom is replaced with a fluorine atom or a chlorine atom, the temperature can be set as lower than the boiling point of the compound that has the lowest boiling point.

The double bond-containing linear hydrocarbon in which every hydrogen atom is replaced with a fluorine atom or a chlorine atom is preferably a linear alkene in which every hydrogen atom is replaced with a fluorine atom or a chlorine atom or a linear alkadiene in which every hydrogen atom is replaced with a fluorine atom or a chlorine atom in terms of stability as a compound resulting from replacement with fluorine or chlorine atoms, and is more preferably a linear perfluoroalkene or a linear perfluoroalkadiene in terms that stability further increases through the electronic structure, electron affinity, and binding energy of fluorine atoms resulting from replacement with only fluorine atoms.

The double bond-containing linear hydrocarbon in which every hydrogen atom is replaced with a fluorine atom or a chlorine atom is preferably a compound having a boiling point of 50° C. or lower in terms that introduction of the compound into a reactor in the form of a gas is easy.

The double bond-containing alicyclic hydrocarbon in which every hydrogen atom is replaced with a fluorine atom or a chlorine atom can be a cycloalkene in which every hydrogen atom is replaced with a fluorine atom or a chlorine atom or a cycloalkadiene in which every hydrogen atom is replaced with a fluorine atom or a chlorine atom, and may be a perfluorocycloalkene or a perfluorocycloalkadiene.

The double bond-containing alicyclic hydrocarbon in which every hydrogen atom is replaced with a fluorine atom or a chlorine atom is preferably a compound having a boiling point of 30° C. or lower in terms that introduction of the compound into a reactor in the form of a gas is easy.

In the presently disclosed method, the tertiary amine of the specific amine compound is preferably a trialkylamine, an N-alkylmorpholine, an N-alkylpiperidine, or an N-alkylpyrrolidine, and the heterocyclic aromatic amine compound of the specific amine compound is preferably pyridine, a derivative of pyridine, pyridazine, a derivative of pyridazine, isoquinoline, or a derivative of isoquinoline. The derivative may be a substituted derivative that is substituted with at least one substituent selected from an alkyl, an alkoxy, an acyl, an alkoxycarbonyl, and an acyloxy.

In the presently disclosed method, the specific amine compound may be the tertiary amine or may be the heterocyclic aromatic amine compound.

In the presently disclosed method, the amount of the amine compound that is used is preferably not less than 0.01 times and not more than 10 times the number of moles of the double bond-containing alicyclic hydrocarbon in which every hydrogen atom is replaced with a fluorine atom or a chlorine atom.

Advantageous Effect

The presently disclosed method is useful in a case in which a linear compound and an alicyclic compound are included among double bond-containing hydrocarbon compounds in which every hydrogen atom is replaced with a fluorine atom or a chlorine atom and makes it possible to selectively separate the linear compound by a simple method of contacting with a specific amine compound.

BRIEF DESCRIPTION OF THE DRAWINGS

In the accompanying drawings.

DETAILED DESCRIPTION (Treatment Subject)

The treatment subject in the presently disclosed method contains a double bond-containing linear hydrocarbon in which every hydrogen atom is replaced with a fluorine atom or a chlorine atom (hereinafter, also referred to as "compound X") and a double bond-containing alicyclic hydrocarbon in which every hydrogen atom is replaced with a fluorine atom or a chlorine atom (hereinafter, also referred to as "compound Y").

<Double Bond-Containing Linear Hydrocarbon in which Every Hydrogen Atom is Replaced with Fluorine Atom or Chlorine Atom (Hereinafter, Also Referred to as "Compound X")>

The compound X, which is a double bond-containing linear hydrocarbon in which every hydrogen atom is replaced with a fluorine atom or a chlorine atom, may be any compound in which every hydrogen atom of a double bond-containing linear hydrocarbon is replaced with either a fluorine atom or a chlorine atom. In the case of replacement with a chlorine atom, it is preferable that one or two hydrogen atoms in the compound X have each been replaced with a chlorine atom and that other hydrogen atoms in the compound X have each been replaced with a fluorine atom.

The boiling point of the compound X is preferably 50° C. or lower, and more preferably 15° C. or lower. The boiling point can be −80° C. or higher.

The number of carbon atoms in the compound X may be 2 or more, and is preferably not less than 2 and not more than 5.

The number of double bonds in the compound X may be 1 or more, and is preferably 1 or 2.

Examples of the compound X that include both chlorine and fluorine atoms include $CF_2=CFCl$, $CFCl=CFCl$, $CF_3CF=CFCl$, $CF_3CCl=CF_2$, $CF_3CCl=CFCl$, and $CF_3CF=CCl_2$.

Examples of the compound X that include only fluorine atoms include linear perfluoroalkenes and linear perfluoroalkadienes. Examples of linear perfluoroalkenes include $CF_2=CF_2$, $CF_3CF=CF_2$, $CF_3CF_2CF=CF_2$, $CF_3CF=CFCF_3$, $CF_3CF_2CF_2CF=CF_2$, $CF_3CF_2CF=CFCF_3$, and the like, and examples of linear perfluoroalkadienes include $CF_2=CFCF=CF_2$, $CF_2=CFCF=CFCF_3$, $CF_2=CFCF_2CF=CF_2$, and the like.

The compound X in the treatment subject may be just one type of compound or may be two or more types of compounds.

<Double Bond-Containing Alicyclic Hydrocarbon in which Every Hydrogen Atom is Replaced with Fluorine Atom or Chlorine Atom (Hereinafter, Also Referred to as "Compound Y")>

The compound Y, which is a double bond-containing alicyclic hydrocarbon in which every hydrogen atom is replaced with a fluorine atom or a chlorine atom, may be any compound in which every hydrogen atom of a double bond-containing alicyclic hydrocarbon is replaced with either a fluorine atom or a chlorine atom. In the case of replacement with a chlorine atom, it is preferable that one or two hydrogen atoms in the compound Y have each been replaced with a chlorine atom and that other hydrogen atoms in the compound Y have each been replaced with a fluorine atom because stability generally increases and reactivity decreases with increasing number of chlorine atoms.

The boiling point of the compound Y is preferably 30° C. or lower, and more preferably 15° C. or lower. The boiling point can be −20° C. or higher.

The number of carbon atoms forming a carbocycle in the compound Y may be 3 or more, and is preferably not less than 3 and not more than 6.

The compound Y may be a monocyclic compound or may be a polycyclic compound, but is preferably a monocyclic compound. The compound Y may include an alkyl group in which every hydrogen atom is replaced with a fluorine atom or a chlorine atom (for example, a perfluoroalkyl group such as a trifluoromethyl group or a pentafluoroethyl group) on the carbocycle.

The number of double bonds in the compound Y may be 1 or more, and is preferably 1 or 2.

Examples of the compound Y that include both chlorine and fluorine atoms include 1-chloropentafluorocyclobutene, 1,2-dichlorotetrafluorocyclobutene, 1,3-dichlorotetrafluorocyclobutene, and the like.

Examples of the compound Y that include only fluorine atoms include perfluorocycloalkenes and perfluorocycloalkadienes. Examples of perfluorocycloalkenes include tetrafluorocyclopropene, hexafluorocyclobutene, octafluorocyclopentene, decafluorocyclohexene, and the like, and examples of perfluorocycloalkadienes include tetrafluorocyclobutadiene, hexafluorocyclopentadiene, octafluoro-1,3-cyclohexadiene, octafluoro-1,4-cyclohexadiene, and the like. These compounds may include an alkyl group in which every hydrogen atom is replaced with a fluorine atom or a chlorine atom (for example, a perfluoroalkyl group such as a trifluoromethyl group or a pentafluoroethyl group) on the carbocycle, and examples of such compounds include 3-trifluoromethyl-pentafluoro-cyclobutene, 3-trifluoromethyl-heptafluoro-cyclopentene, 4-trifluoromethyl-heptafluoro-cyclopentene, and the like.

The compound Y in the treatment subject may be just one type of compound or may be two or more types of compounds.

<Mixing Ratio>

Although no specific limitations are placed on the proportions of the compound X and the compound Y in the treatment subject, a mass ratio thereof (mass of compound X:mass of compound Y) can be 0.1:99.9 to 99.9:0.1, for example. From a viewpoint of obtaining a sufficient separation effect and easily collecting the compound X after separation, the mass ratio of the compound X and the compound Y (mass of compound X:mass of compound Y) is preferably 1:9 to 9:1, and more preferably 3:7 to 7:3.

<Other Components>

The treatment subject may contain other components to the extent that the effects of the presently disclosed method are not lost. Examples of such other components include nitrogen, helium, argon, atmospheric air, aliphatic saturated hydrocarbons, ethers, aromatic hydrocarbons, and the like. Other components are preferably 99 mol % or less, and more preferably 50 mol % or less relative to the overall treatment subject. Moreover, other components may be 0%, in which case, the treatment subject is composed of the compound X and the compound Y. The treatment subject should contain the compound X and the compound Y at the time when it is brought into contact with a specific amine compound.

(Specific Amine Compound)

The presently disclosed method uses at least one amine compound selected from the group consisting of a heterocyclic aromatic amine compound and a tertiary amine represented by a formula: $NR^1R^2R^3$ ($R^1$, $R^2$ and $R^3$ are each independently an alkyl group, and two among $R^1$, $R^2$, and $R^3$ may in combination form an alkylene group that is optionally interrupted by an oxygen atom or a sulfur atom). The amine compound may be the tertiary amine, may be the heterocyclic aromatic amine compound, or may be a combination thereof.

The specific amine compound is preferably a liquid at room temperature (23° C.) under atmospheric pressure. The melting point of the specific amine is preferably −120° C. or higher, and more preferably −50° C. or higher, and is preferably 50° C. or lower, and more preferably 30° C. or lower.

<Tertiary Amine>

The tertiary amine is represented by a formula: $NR^1R^2R^3$ ($R^1$, $R^2$ and $R^3$ are each independently an alkyl group, and two among $R^1$, $R^2$, and $R^3$ may in combination form an alkylene group that is optionally interrupted by an oxygen atom or a sulfur atom).

In a case in which $R^1$, $R^2$, and $R^3$ are each an alkyl group, these alkyl groups may be the same or may be different, but are preferably the same.

The alkyl group may be linear or may be branched. The alkyl group may be an alkyl group in which the number of carbon atoms is not less than 1 and not more than 4, and is preferably an alkyl group in which the number of carbon atoms is not less than 1 and not more than 3, examples of which include methyl, ethyl, and propyl.

Two among $R^1$, $R^2$, and $R^3$ may in combination form an alkylene group that is optionally interrupted by an oxygen atom or a sulfur atom, examples of which include a —$(CH_2)_p$— group (p is an integer of not less than 3 and not more than 6), a —$(CH_2)_q$—O—$(CH_2)_q$— group (q is an integer of not less than 1 and not more than 3, and each q may be the same or may be different), a —$(CH_2)_r$—S—$(CH_2)_r$— group (r is an integer of not less than 1 and not more than 3, and each r may be the same or may be different), and the like. The remaining one of $R^1$, $R^2$, and $R^3$ is an alkyl group, and examples and preferable examples of the alkyl group are as described above.

The tertiary amine is preferably a trialkylamine such as triethylamine or methyldiethylamine, an N-alkylmorpholine such as N-methylmorpholine, N-ethylmorpholine, or N-butylmorpholine, an N-alkylpiperidine such as N-methylpiperidine or N-ethylpiperidine, an N-alkylpyrrolidine such as N-methylpyrrolidine or N-ethylpyrrolidine, or the like.

<Heterocyclic Aromatic Amine Compound>

The heterocyclic aromatic amine compound may be a monocyclic compound or may be a polycyclic compound, but is preferably a monocyclic compound. It is preferable that a hydrogen atom is not present on a nitrogen atom that is a ring-forming atom of the heteroaromatic ring.

Examples of the heterocyclic aromatic amine compound include pyridine, pyrazine, pyrimidine, pyridazine, quinoline, isoquinoline, bipyridine, and derivatives thereof. The derivative may be a substituted derivative, with examples of possible substituents including an alkyl, an alkoxy, an acyl, an alkoxycarbonyl, an acyloxy, a cyano, and the like. The derivative may include one substituent or may include two or more substituents.

An alkyl part in any of the substituents mentioned above may be linear or may be branched, and the number of carbon atoms included therein is preferably not less than 1 and not more than 5. The alkyl may be methyl, ethyl, propyl, butyl, or the like, the alkoxy may be methoxy, ethoxy, propoxy, butoxy, or the like, the acyl may be acetyl, propionyl, or the like, the alkoxycarbonyl may be methoxycarbonyl, ethoxycarbonyl, or the like, and the acyloxy may be acetyloxy, propionyloxy, or the like.

The heterocyclic aromatic amine compound is preferably pyridine, a derivative of pyridine, pyridazine, a derivative of pyridazine, isoquinoline or a derivative of isoquinoline.

(Contacting Step)

No specific limitations are placed on the method by which the treatment subject and the specific amine compound are brought into contact. For example, the treatment subject may be added into a reactor that contains the specific amine compound or the treatment subject may be introduced into a specific reactor and then the specific amine may subsequently be injected into the reactor.

Contacting of the treatment subject and the specific amine compound is preferably performed with the specific amine compound in the form of a liquid. For example, the specific amine compound can be brought into contact with the treatment subject as a liquid by adjusting the temperature of the specific amine compound to not lower than the melting point thereof or by dissolving or dispersing the specific amine compound in a solvent (for example, an aliphatic saturated hydrocarbon, an ether, an aromatic hydrocarbon, or the like).

The treatment subject can be introduced into a reactor in the form of a gas. The treatment subject may be subjected to heating or the like to place it in the form of a gas. After the treatment subject has been introduced into the reactor, the treatment subject may be brought into contact with the specific amine compound in a gas phase or may be partially or fully liquified through cooling inside the reactor and be brought into contact with the specific amine compound in a liquid phase.

The treatment subject is preferably brought into contact with the specific amine compound at a lower temperature than the boiling point of the compound Y in the treatment subject. In a case in which a plurality of compounds Y are present, the temperature can be set as lower than the boiling point of the compound Y that has the lowest boiling point.

The contact time of the treatment subject and the specific amine compound is not specifically limited but can be set as not less than 1 hour and not more than 24 hours, for example, and is preferably not less than 5 hours and not more than 18 hours. The reaction time can be shortened by performing stirring of the inside of the reactor during contacting.

After contacting has been performed for a specific time, gas inside the reactor is captured, and reaction product produced as a result of the contacting is collected. The compound X separates into the gas that is captured.

The number of moles of the specific amine compound can be set as not less than 0.01 times and not more than 10 times, and preferably not less than 0.03 times and not more than 5.0 times the number of moles of the compound Y in the treatment subject. In a case in which the specific amine compound is the tertiary amine, this number of moles is preferably 0.5 times or more, and more preferably 1.0 times or more, and is preferably 4.0 times or less, and more preferably 3.0 times or less. In a case in which the specific amine compound is the heterocyclic aromatic amine compound, this number of moles is preferably 0.05 times or more, and more preferably 0.1 times or more, and is preferably 3.0 times or less, and more preferably 2.0 times or less.

By using the presently disclosed separation method, it is possible to obtain the double bond-containing linear hydrocarbon in which every hydrogen atom is replaced with a fluorine atom or a chlorine atom with a trace amount of the specific amine compound contained therein. As a result of a trace amount of the specific amine compound remaining in the double bond-containing linear hydrocarbon in which every hydrogen atom is replaced with a fluorine atom or a chlorine atom, gas detection is possible through odor of the specific amine compound. For example, the double bond-containing linear hydrocarbon in which every hydrogen atom is replaced with a fluorine atom or a chlorine atom may, in a gas phase, contain not less than 0.001 volume ppm and not more than 1,000 volume ppm of at least one amine compound selected from the group consisting of a heterocyclic aromatic amine compound and a tertiary amine represented by a formula: $NR^1R^2R^3$ ($R^1$, $R^2$ and $R^3$ are each independently an alkyl group, and two among $R^1$, $R^2$, and $R^3$ may in combination form an alkylene group that is optionally interrupted by an oxygen atom or a sulfur atom).

EXAMPLES

The following provides a more specific description of the present disclosure based on examples. However, the present disclosure is not limited to the following examples.

In each of the examples, a specific amine compound, a double bond-containing linear hydrocarbon in which every hydrogen atom is replaced with a fluorine atom or a chlorine atom (compound X), and a double bond-containing alicyclic hydrocarbon in which every hydrogen atom is replaced with a fluorine atom or a chlorine atom (compound Y) that are indicated in Table 1 were used.

$CF_2=CFCl$ (boiling point −28° C.)
$CF_3CF=CF_2$ (boiling point −29° C.)
$CF_3CF=CFCF_3$ (boiling point 1.2° C.)
$CF_3CF_2CF=CF_2$ (boiling point 6° C.)
$CF_2=CFCF=CF_2$ (boiling point 5° C. to 6° C.)
c-$C_4F_6$: Hexafluorocyclobutene (boiling point 5° C. to 6° C.)
c-$C_5F_8$: Octafluorocyclopentene (boiling point 27° C.)

A first pressure-resistant vessel that had been internally depressurized and cooled to −20° C. to −40° C. was supplied with the compound X and the compound Y as a gas in a mass ratio indicated in Table 1 via a valve connected to the first pressure-resistant vessel, and then the specific amine compound was subsequently charged to the first pressure-resistant vessel. With regards to the used amount of the specific amine compound, the amount corresponding to the number of moles relative to 1 mol of the compound Y is shown in Table 1. The first pressure-resistant vessel was loaded into a thermostatic tank having a temperature indicated in Table 1 and was left overnight (14 hours) while the inside of the vessel was being stirred.

Thereafter, a second pressure-resistant vessel that had been internally depressurized and cooled to −20° C. to −60° C. was connected to the first pressure-resistant vessel, valves of these vessels were opened, and gas remaining in the first pressure-resistant vessel was transferred to the second pressure-resistant vessel. Next, the first pressure-resistant vessel was gradually heated to 30° C. over 30 minutes. The valves of the vessels were then closed, and the mass of residue in the first pressure-resistant vessel and the mass of gas captured in the second pressure-resistant vessel were determined.

The first pressure-resistant vessel and the second pressure-resistant vessel were subsequently each cooled to −20° C. to −40° C., deuterated chloroform for NMR analysis was loaded into each of the vessels, and compounds inside the vessels were dissolved and then taken out under cooling in order to perform fluorine NMR measurement thereof.

Measurement conditions: $^{19}$F-NMR measurement (376 MHz, $CDCl_3$, trifluoromethyltoluene added as internal standard)

Figure 1:
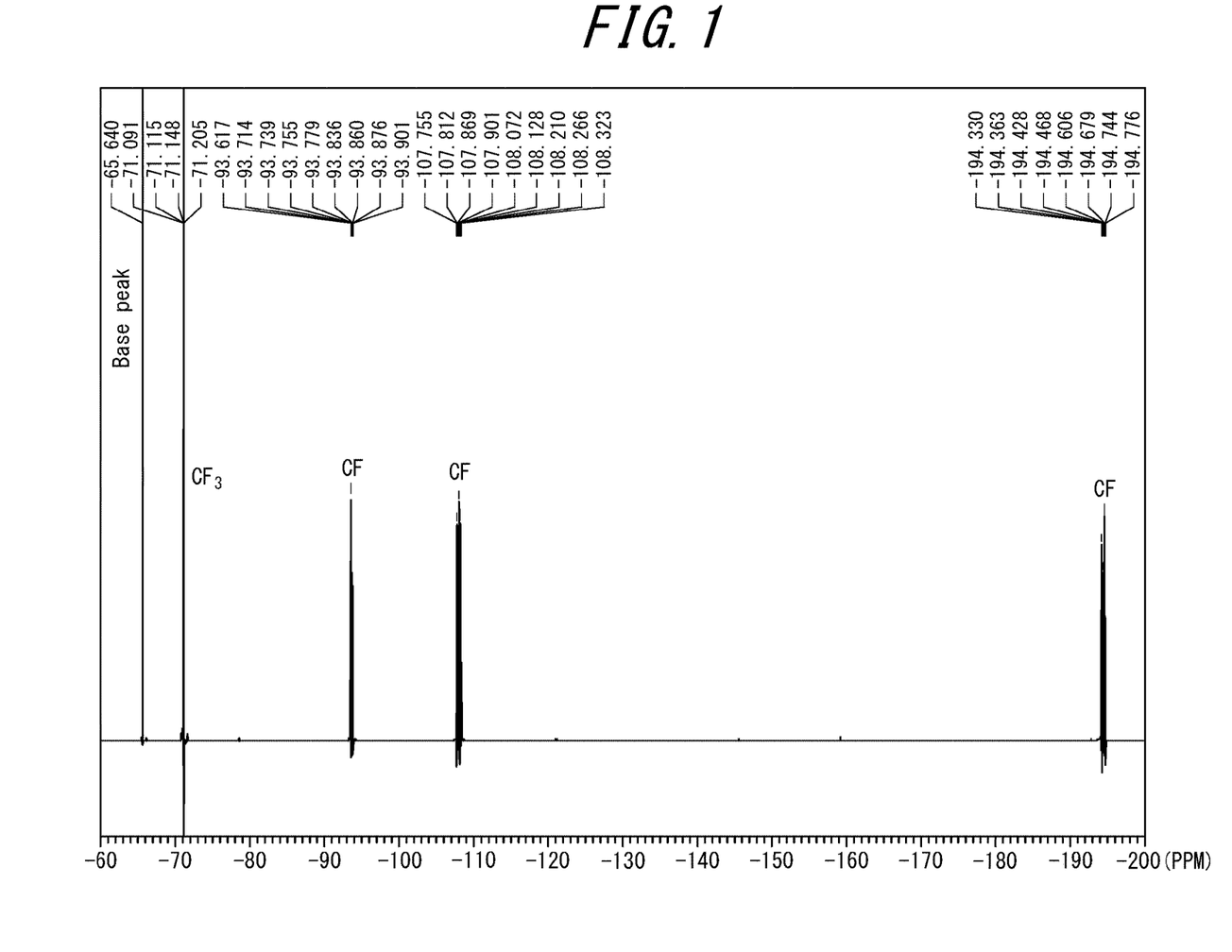
FIG. 1 illustrates results of fluorine NMR measurement of compounds inside a second pressure-resistant vessel in Example 12.

The results of fluorine NMR measurement in Example 12 are illustrated in FIG. 1.

FIG. 1 illustrates measurement results for compounds inside the second pressure-resistant vessel. The corresponding peaks are peaks originating from $CF_3CF=CF_2$. Note that peaks for c-$C_4F_6$ (−122.2 ppm ($CF_2$) and −131.0 ppm (CF)) were not detected.

Figure 2:
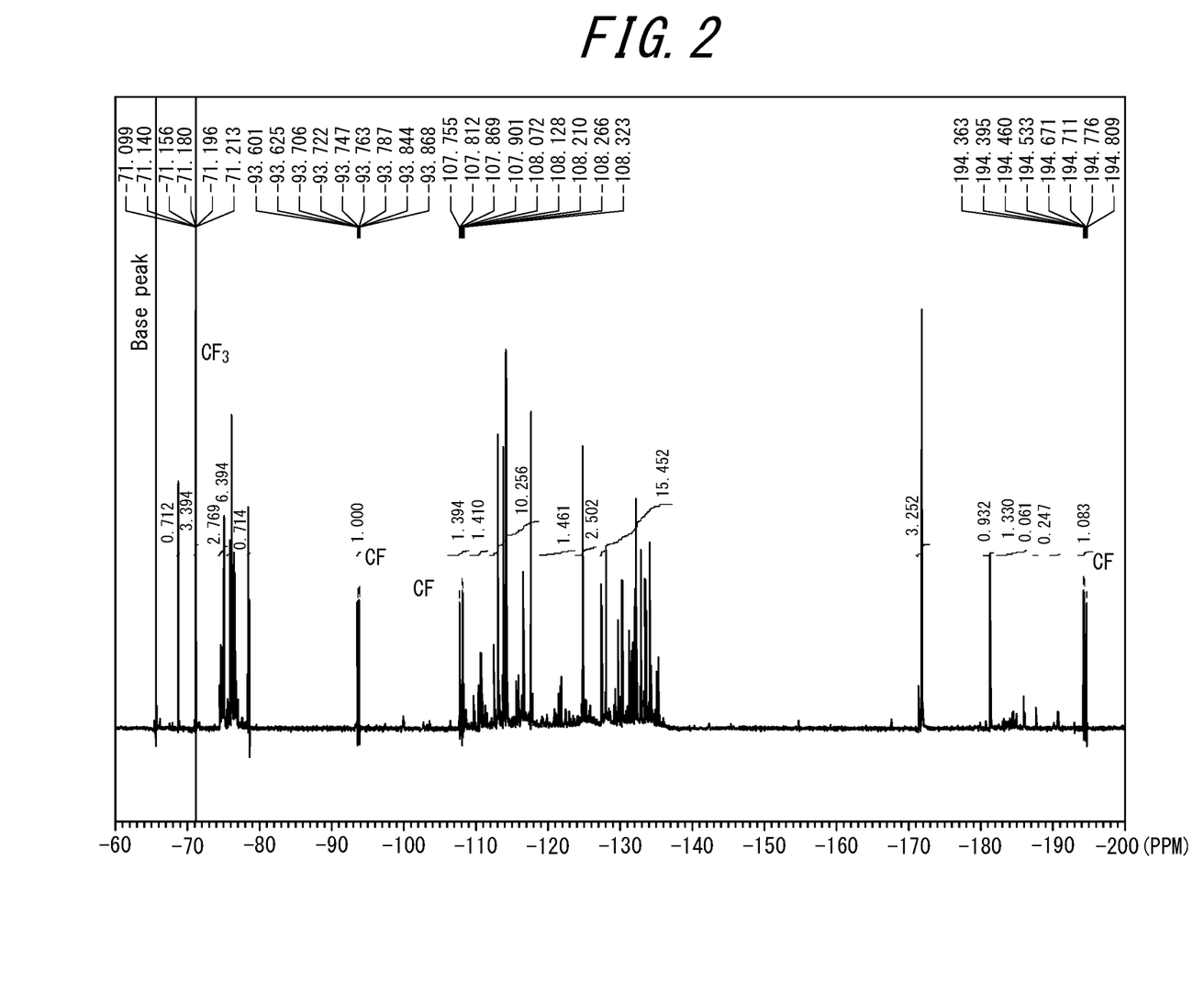
FIG. 2 illustrates results of fluorine NMR measurement of compounds inside a first pressure-resistant vessel in Example 12.

FIG. 2 illustrates measurement results for compounds inside the first pressure-resistant vessel. Peaks for c-$C_4F_6$ were not detected, and peaks other than those originating from $CF_3CF=CF_2$ are presumed to originate from a reaction product.

The proportions of the compound X, compound Y, and reaction product inside each of the pressure-resistant vessels were calculated from integrated values of peaks for the compound X, compound Y, and reaction product in fluorine NMR measurement, and a conversion rate of the compound Y and a non-conversion rate of the compound X were calculated from the mass of the residue and the mass of the captured gas that were previously determined.

The conversion rate of the compound Y is the proportion by which the compound Y is reduced after contacting relative to the charged amount of the compound Y. The conversion rate was evaluated as follows.

Conversion Rate of Compound Y

| | |
|---|---|
| Conversion rate: 80% or more | A |
| Conversion rate: Not less than 20% and less than 80% | B |
| Conversion rate: Less than 20% | C |
| Conversion rate: No reaction product | D |

The non-conversion rate of the compound X is the proportion of the compound X that remains after contacting relative to the charged amount of the compound X. The non-conversion rate was evaluated as follows.

Non-Conversion Rate of Compound X

| | |
|---|---|
| Non-conversion rate: 99% or more | A |
| Non-conversion rate: Not less than 95% and less than 99% | B |
| Non-conversion rate: Less than 95% | C |

Separation of the compound X was considered to have been achieved in a case in which the conversion rate was A or B and the non-conversion rate was A or B. The results are shown in Table 1.

TABLE 1

| Example | Compound X | Compound Y | Specific amine compound | Mass ratio compound X: compound Y | No. of moles of specific amine compound relative to 1 mol of compound Y | Thermostatic tank | Conversion rate | Non-conversion rate |
|---|---|---|---|---|---|---|---|---|
| 1 | $CF_2=CFCl$ | c-$C_4F_6$ | Triethylamine | 1:1 | 1.5 | 0° C. | A | A |
| 2 | $CF_2=CFCl$ | c-$C_5F_8$ | Triethylamine | 1:1 | 1.5 | 0° C. | A | A |
| 3 | $CF_3CF=CF_2$ | c-$C_4F_6$ | Triethylamine | 1:1 | 1.5 | 0° C. | A | B |
| 4 | $CF_3CF=CF_2$ | c-$C_5F_8$ | Triethylamine | 1:1 | 1.5 | 0° C. | A | B |
| 5 | $CF_3CF=CFCF_3$ | c-$C_4F_6$ | Triethylamine | 1:1 | 1.5 | 0° C. | A | A |
| 6 | $CF_3CF_2CF=CF_2$ | c-$C_4F_6$ | Triethylamine | 1:1 | 1.5 | 0° C. | A | A |
| 7 | $CF_2=CFCF=CF_2$ | c-$C_5F_8$ | Triethylamine | 1:1 | 1.5 | 0° C. | A | A |
| 8 | $CF_2=CFCF=CF_2$ | c-$C_5F_8$ | Triethylamine | 1:1 | 1.5 | 25-35° C. | A | A |
| 9 | $CF_2=CFCl$ | c-$C_4F_6$ | 4-Ethylmorpholine | 1:1 | 1.5 | 0° C. | B | A |
| 10 | $CF_3CF=CFCF_3$ | c-$C_4F_6$ | 4-Ethylmorpholine | 1:1 | 1.5 | 0° C. | B | A |
| 11 | $CF_2=CFCl$ | c-$C_5F_8$ | Pyridine | 1:1 | 1.5 | 0° C. | A | A |
| 12 | $CF_3CF=CF_2$ | c-$C_4F_6$ | Pyridine | 1:1 | 0.5 | 0° C. | A | A |
| 13 | $CF_3CF=CF_2$ | c-$C_4F_6$ | Pyridine | 1:1 | 0.5 | 20-23° C. | A | A |
| 14 | $CF_3CF=CF_2$ | c-$C_4F_6$ | Pyridine | 1:9 | 0.5 | 0° C. | A | A |
| 15 | $CF_3CF=CF_2$ | c-$C_5F_8$ | Pyridine | 1:1 | 1.5 | 0° C. | A | A |
| 16 | $CF_3CF=CFCF_3$ | c-$C_4F_6$ | Pyridine | 9:1 | 0.5 | 0° C. | A | A |

TABLE 1-continued

| Example | Compound X | Compound Y | Specific amine compound | Mass ratio compound X: compound Y | No. of moles of specific amine compound relative to 1 mol of compound Y | Thermostatic tank | Conversion rate | Non-conversion rate |
|---|---|---|---|---|---|---|---|---|
| 17 | $CF_3CF=CFCF_3$ | $c\text{-}C_5F_8$ | Pyridine | 1:1 | 1.5 | 0° C. | A | A |
| 18 | $CF_2=CFCF=CF_2$ | $c\text{-}C_4F_6$ | Pyridine | 1:1 | 0.5 | 0° C. | A | A |
| 19 | $CF_2=CFCF=CF_2$ | $c\text{-}C_4F_6$ | Pyridine | 1:1 | 1.5 | 25-35° C. | A | A |
| 20 | $CF_2=CFCl$ | $c\text{-}C_4F_6$ | 4-Methylpyridine | 1:1 | 1.5 | 0° C. | A | A |
| 21 | $CF_2=CFCl$ | $c\text{-}C_5F_8$ | 4-Methylpyridine | 1:1 | 1.5 | 0° C. | A | A |
| 22 | $CF_3CF=CF_2$ | $c\text{-}C_4F_6$ | 4-Methylpyridine | 1:1 | 1.5 | 0° C. | A | A |
| 23 | $CF_2=CFCF=CF_2$ | $c\text{-}C_4F_6$ | 4-Methylpyridine | 1:1 | 1.5 | 0° C. | A | A |
| 24 | $CF_2=CFCF=CF_2$ | $c\text{-}C_5F_8$ | 4-Methylpyridine | 1:1 | 1.0 | 25-35° C. | A | A |
| 25 | $CF_3CF=CF_2$ | $c\text{-}C_5F_8$ | 4-Methylpyridine | 1:1 | 1.5 | 0° C. | A | A |
| 26 | $CF_2=CFCF=CF_2$ | $c\text{-}C_5F_8$ | 4-Methylpyridine | 1:1 | 1.5 | 0° C. | A | A |
| 27 | $CF_2=CFCl$ | $c\text{-}C_4F_6$ | 3,4-Dimethylpyridine | 1:1 | 1.5 | 0° C. | A | A |
| 28 | $CF_3CF=CFCF_3$ | $c\text{-}C_4F_6$ | 3,4-Dimethylpyridine | 1:1 | 1.5 | 0° C. | A | A |
| 29 | $CF_3CF=CFCF_3$ | $c\text{-}C_5F_8$ | 3,4-Dimethylpyridine | 1:1 | 1.5 | 0° C. | A | A |
| 30 | $CF_3CF_2CF=CF_2$ | $c\text{-}C_4F_6$ | 3,4-Dimethylpyridine | 1:1 | 1.5 | 0° C. | A | A |
| 31 | $CF_3CF_2CF=CF_2$ | $c\text{-}C_5F_8$ | 3,4-Dimethylpyridine | 1:1 | 1.5 | 0° C. | A | A |
| 32 | $CF_2=CFCF=CF_2$ | $c\text{-}C_5F_8$ | 3,4-Dimethylpyridine | 1:1 | 1.5 | 0° C. | A | A |
| 33 | $CF_2=CFCF=CF_2$ | $c\text{-}C_5F_8$ | 3,4-Dimethylpyridine | 1:1 | 0.5 | 25-35° C. | A | A |
| 34 | $CF_3CF=CF_2$ | $c\text{-}C_4F_6$ | 4-Acetylpyridine | 1:1 | 1.5 | 20-23° C. | A | B |
| 35 | $CF_2=CFCF=CF_2$ | $c\text{-}C_5F_8$ | 4-Acetylpyridine | 1:1 | 1.5 | 20-23° C. | A | A |
| 36 | $CF_2=CFCF=CF_2$ | $c\text{-}C_5F_8$ | Ethyl isonicotinate | 1:1 | 1.5 | 0° C. | B | A |
| 37 | $CF_3CF=CF_2$ | $c\text{-}C_4F_6$ | Pyridazine | 1:1 | 1.5 | 0° C. | A | A |
| 38 | $CF_3CF=CF_2$ | $c\text{-}C_5F_8$ | Pyridazine | 1:1 | 1.5 | 0° C. | A | A |
| 39 | $CF_2=CFCF=CF_2$ | $c\text{-}C_5F_8$ | Pyridazine | 1:1 | 1.5 | 0° C. | A | A |
| 40 | $CF_3CF=CF_2$ | $c\text{-}C_4F_6$ | Isoquinoline | 1:1 | 1.5 | 20-23° C. | A | B |
| 41 | $CF_2=CFCF=CF_2$ | $c\text{-}C_4F_6$ | Isoquinoline | 1:1 | 0.5 | 25-35° C. | A | A |
| 42 | $CF_2=CFCF=CF_2$ | $c\text{-}C_5F_8$ | Isoquinoline | 1:1 | 1.5 | 20-23° C. | A | A |
| 43 | $CF_2=CFCF=CF_2$ | $c\text{-}C_5F_8$ | Isoquinoline | 1:1 | 1.0 | 25-35° C. | A | A |

INDUSTRIAL APPLICABILITY

The presently disclosed method is useful in a case which a linear compound and an alicyclic compound are included among double bond-containing hydrocarbon compounds in which every hydrogen atom is replaced with a fluorine atom or a chlorine atom and makes it possible to selectively separate the linear compound by a simple method of contacting with a specific amine compound.

The invention claimed is:

1. A method of separating a double bond-containing linear hydrocarbon in which every hydrogen atom is replaced with a fluorine atom or a chlorine atom, comprising bringing a treatment subject containing a double bond-containing linear hydrocarbon in which every hydrogen atom is replaced with a fluorine atom or a chlorine atom and a double bond-containing alicyclic hydrocarbon in which every hydrogen atom is replaced with a fluorine atom or a chlorine atom into contact with at least one amine compound selected from the group consisting of a heterocyclic aromatic amine compound and a tertiary amine represented by a formula: $NR^1R^2R^3$, where $R^1$, $R^2$, and $R^3$ are each independently an alkyl group, and two among $R^1$, $R^2$, and $R^3$ may in combination form an alkylene group that is optionally interrupted by an oxygen atom or a sulfur atom.

2. The method of separating a double bond-containing linear hydrocarbon in which every hydrogen atom is replaced with a fluorine atom or a chlorine atom according to claim 1, wherein the amine compound that the treatment subject is brought into contact with is in the form of a liquid.

3. The method of separating a double bond-containing linear hydrocarbon in which every hydrogen atom is replaced with a fluorine atom or a chlorine atom according to claim 1, wherein contacting of the treatment subject and the amine compound is performed inside a reactor, and the treatment subject is introduced into the reactor in the form of a gas.

4. The method of separating a double bond-containing linear hydrocarbon in which every hydrogen atom is replaced with a fluorine atom or a chlorine atom according to claim 1, wherein the treatment subject is brought into contact with the amine compound at a lower temperature than a boiling point of the double bond-containing alicyclic hydrocarbon in which every hydrogen atom is replaced with a fluorine atom or a chlorine atom.

5. The method of separating a double bond-containing linear hydrocarbon in which every hydrogen atom is replaced with a fluorine atom or a chlorine atom according to claim 1, wherein the double bond-containing linear hydrocarbon in which every hydrogen atom is replaced with a fluorine atom or a chlorine atom is a linear alkene in which every hydrogen atom is replaced with a fluorine atom or a chlorine atom or a linear alkadiene in which every hydrogen atom is replaced with a fluorine atom or a chlorine atom.

6. The method of separating a double bond-containing linear hydrocarbon in which every hydrogen atom is replaced with a fluorine atom or a chlorine atom according to claim 5, wherein the double bond-containing linear hydrocarbon in which every hydrogen atom is replaced with a fluorine atom or a chlorine atom is a linear perfluoroalkene or a linear perfluoroalkadiene.

7. The method of separating a double bond-containing linear hydrocarbon in which every hydrogen atom is replaced with a fluorine atom or a chlorine atom according to claim 1, wherein the double bond-containing linear hydrocarbon in which every hydrogen atom is replaced with a fluorine atom or a chlorine atom is a compound having a boiling point of 50° C. or lower.

8. The method of separating a double bond-containing linear hydrocarbon in which every hydrogen atom is replaced with a fluorine atom or a chlorine atom according to claim 1, wherein the double bond-containing alicyclic hydrocarbon in which every hydrogen atom is replaced with a fluorine atom or a chlorine atom is a cycloalkene in which every hydrogen atom is replaced with a fluorine atom or a chlorine atom or a cycloalkadiene in which every hydrogen atom is replaced with a fluorine atom or a chlorine atom.

9. The method of separating a double bond-containing linear hydrocarbon in which every hydrogen atom is replaced with a fluorine atom or a chlorine atom according to claim 8, wherein the double bond-containing alicyclic hydrocarbon in which every hydrogen atom is replaced with a fluorine atom or a chlorine atom is a perfluorocycloalkene or a perfluorocycloalkadiene.

10. The method of separating a double bond-containing linear hydrocarbon in which every hydrogen atom is replaced with a fluorine atom or a chlorine atom according to claim 1, wherein the double bond-containing alicyclic hydrocarbon in which every hydrogen atom is replaced with a fluorine atom or a chlorine atom is a compound having a boiling point of 30° C. or lower.

11. The method of separating a double bond-containing linear hydrocarbon in which every hydrogen atom is replaced with a fluorine atom or a chlorine atom according to claim 1, wherein the tertiary amine is a trialkylamine, an N-alkylmorpholine, an N-alkylpiperidine, or an N-alkylpyrrolidine, and the heterocyclic aromatic amine compound is pyridine, a derivative of pyridine, pyridazine, a derivative of pyridazine, isoquinoline, or a derivative of isoquinoline.

12. The method of separating a double bond-containing linear hydrocarbon in which every hydrogen atom is replaced with a fluorine atom or a chlorine atom according to claim 1, wherein the amine compound is the tertiary amine.

13. The method of separating a double bond-containing linear hydrocarbon in which every hydrogen atom is replaced with a fluorine atom or a chlorine atom according to claim 1, wherein the amine compound is the heterocyclic aromatic amine compound.

14. The method of separating a double bond-containing linear hydrocarbon in which every hydrogen atom is replaced with a fluorine atom or a chlorine atom according to claim 1, wherein the number of moles of the amine compound that is used is not less than 0.01 times and not more than 10 times the number of moles of the double bond-containing alicyclic hydrocarbon in which every hydrogen atom is replaced with a fluorine atom or a chlorine atom.

* * * * *